US011999984B2

(12) United States Patent
Huang et al.

(10) Patent No.: US 11,999,984 B2
(45) Date of Patent: Jun. 4, 2024

(54) METHOD AND SPECIAL COMPLEX ENZYME FOR HYDROLYZING GALACTOMANNAN (GM) TO PREPARE SMALL-MOLECULE GM AND GALACTOMANNAN OLIGOSACCHARIDE (GMOS)

(71) Applicant: NANJING FORESTRY UNIVERSITY, Nanjing (CN)

(72) Inventors: Caoxing Huang, Nanjing (CN); Qiang Yong, Nanjing (CN); Yuheng Tao, Nanjing (CN); Chenhuan Lai, Nanjing (CN); Yong Xu, Nanjing (CN); Xin Li, Nanjing (CN)

(73) Assignee: NANJING FORESTRY UNIVERSITY, Nanjing (CN)

( * ) Notice: Subject to any disclaimer, the term of this patent is extended or adjusted under 35 U.S.C. 154(b) by 0 days.

(21) Appl. No.: 18/274,770

(22) PCT Filed: May 6, 2021

(86) PCT No.: PCT/CN2021/091850
§ 371 (c)(1),
(2) Date: Jul. 28, 2023

(87) PCT Pub. No.: WO2022/160495
PCT Pub. Date: Aug. 4, 2022

(65) Prior Publication Data
US 2024/0035056 A1    Feb. 1, 2024

(30) Foreign Application Priority Data
Jan. 29, 2021  (CN) .......................... 202110129322.6

(51) Int. Cl.
C12P 19/04    (2006.01)
C12N 9/24    (2006.01)
(Continued)

(52) U.S. Cl.
CPC ............ *C12P 19/04* (2013.01); *C12N 9/2465* (2013.01); *C12N 9/2491* (2013.01); *C12Y 302/01022* (2013.01); *C12Y 302/01025* (2013.01)

(58) Field of Classification Search
CPC ...... C12N 9/2465; C12N 9/2491; C12P 19/04
See application file for complete search history.

(56) References Cited

FOREIGN PATENT DOCUMENTS

| CN | 104846035 A | 8/2015 |
|----|-------------|--------|
| CN | 106282142 A | 1/2017 |

OTHER PUBLICATIONS

Malgas. A review of the enzymatic hydrolysis of mannans and synergistic interactions between β-mannanase, β-mannosidase and α-galactosidase. World J Microbiol Biotechnol 31, 1167-1175 (2015).*

(Continued)

*Primary Examiner* — Yong D Pak
(74) *Attorney, Agent, or Firm* — Bayramoglu Law Offices LLC

(57) ABSTRACT

A method and special complex enzyme for hydrolyzing a galactomannan (GM) to prepare a small-molecule GM and a galactomannan oligosaccharide (GMOS) is provided. The method includes: conducting fermentation with microcrystalline cellulose (MCC) and melibiose as carbon sources and *Trichoderma reesei* (*T. reesei*) as an enzyme-producing strain to obtain a supernatant, which is a complex enzyme solution with enzymatic activities of β-mannanase and α-galactosidase; and directly using the complex enzyme solution for enzymatic hydrolysis of a GM as a substrate to prepare the small-molecule GM and the GMOS.

8 Claims, 4 Drawing Sheets

(51) Int. Cl.
  *C12N 9/26* (2006.01)
  *C12N 9/40* (2006.01)

(56) References Cited

OTHER PUBLICATIONS

Yan. Using One-pot Fermentation Technology to Prepare Enzyme Cocktail to Sustainably Produce Low Molecular Weight Galactomannans from Sesbania cannabina Seeds. Appl Biochem Biotechnol. Jul. 2022;194(7):3016-3030.*

Wang Jing, et al., Effects of medium components on β mannanase production by Trichoderma reesei, Journal of Nanjing Forestry University (Natural Science Edition), 2013, pp. 101-104, vol. 31 No. 1.

Susanne Zeilinger, et al., Conditions of Formation, Purification, and Characterization of an α-Galactosidase of Trichoderma reesei RUT C-30, Applied and Environmental Microbiology, 1993, pp. 1347-1353, vol. 59 No.5.

Heli Ji, China Food Additives and Ingredients User Manual, 2016, pp. 268, China Quality Inspection Press.

Nairui Huo, et al., Microbial Biology, 2018, pp. 389, China Agricultural University Press.

* cited by examiner

METHOD AND SPECIAL COMPLEX ENZYME FOR HYDROLYZING GALACTOMANNAN (GM) TO PREPARE SMALL-MOLECULE GM AND GALACTOMANNAN OLIGOSACCHARIDE (GMOS)

CROSS REFERENCE TO THE RELATED APPLICATIONS

This application is the national phase entry of International Application No. PCT/CN2021/091850, filed on May 6, 2021, which is based upon and claims priority to Chinese Patent Application No. 202110129322.6, filed on Jan. 29, 2021, the entire contents of which are incorporated herein by reference.

TECHNICAL FIELD

The present disclosure belongs to the technical field of microorganism cultivation, and specifically relates to a method and special complex enzyme for hydrolyzing a galactomannan (GM) to prepare a small-molecule GM (GM with a molecular weight of 20,000 or less) and a galactomannan oligosaccharide (GMOS).

BACKGROUND

The population aging and the increasingly-young disease populations in China have caused people to pay attention to health issues. In 2016, China issued the "Outline of the Healthy China 2030 Plan" to develop the health industry and improve people's health in China. Dietary fiber has become one of the research hotspots in the context of "Healthy China" due to its unique physiological functions. Dietary fiber includes natural polysaccharides, oligosaccharides, and small-molecule glycans. The oligosaccharides and small-molecule glycans have attracted more and more attention due to their outstanding effects of facilitating the proliferation of intestinal beneficial bacteria, increasing intestinal biodiversity, and enhancing immunity. Generally, small-molecule glycans and oligosaccharides are produced through the degradation of polysaccharides. Therefore, how to increase the content of a component with a low polymerization degree has become one of the key technologies for the preparation of small-molecule glycans and oligosaccharides.

Small-molecule GMs and GMOSs have attracted more attention due to their excellent immune enhancement effects. Generally, the main production technologies to prepare small-molecule GMs and GMOSs include: dilute acid hydrolysis technology, enzymatic hydrolysis technology, physical degradation technology, and combined degradation technology. The enzymatic hydrolysis technology is increasingly favored due to mild preparation conditions by enzyme, high selectivity, strong controllability, and simplified product separation and purification procedures. The use of a microbial fermentation technology to control the synthesis of an enzyme component can also effectively control the generation of by-products, thereby simplifying an extraction process and production cost. Therefore, the production of small-molecule GMs and GMOSs based on the enzymatic hydrolysis process has promising development prospects. In the current method for preparation of a small-molecule GM and a GMOS by enzyme, GM-containing locust bean gum, fenugreek gum, *sesbania* gum, *Gleditsia microphylla*, or the like is adopted as a raw material, and partial enzymatic hydrolysis is conducted under an action of β-mannanase. In general, a β-mannanase system obtained from a microbial fermentation process is a complex enzyme system composed of β-mannanase (also known as endo-β-mannanase) and β-mannosidase, where the β-mannanase mainly degrades β-1,4-glycosidic bonds on a GM backbone to degrade a macromolecular polysaccharide into small molecules; and the β-mannosidase degrades a small-molecule polysaccharide or an oligosaccharide into a monosaccharide. Therefore, the presence of β-mannosidase will increase the content of monosaccharides in a degradation product and decrease yields of the small-molecule GM and GMOS. As a result, in a reaction system to prepare a small-molecule GM and a GMOS through degradation of a GM by β-mannanase, a content of β-mannosidase (which is usually expressed by an enzymatic activity) should be as low as possible.

A GM is a polymer with a high branching degree, where a backbone structure is formed by mannose through a β-1,4-glycosidic bond, and galactose is linked to the backbone structure through an α-1,6-glycosidic bond. For example, in a GM molecule derived from a *sesbania* seed, a molar ratio of a mannose molecule to a galactose molecule is 1.6, that is, 2 galactose molecules are on average linked to every 3 mannose molecules on a backbone. In the process of degrading a GM by β-mannanase, a galactose branched chain causes a steric hindrance effect for β-mannanase to hinder the degradation of β-mannanase, which is specifically manifested as low proportions of high-bioactivity small-molecule glycan and GMOS components in a GM degradation product.

A strategy to avoid a steric hindrance effect caused by a galactose branched chain for β-mannanase during the degradation of a GM with a high branching degree by β-mannanase to prepare a small-molecule GM and a GMOS is to add an appropriate amount of α-galactosidase in the enzymatic hydrolysis system with a β-mannanase. α-Galactosidase is an enzyme that can specifically hydrolyze the α-1,6-glycosidic bond formed between mannose and galactose in a GM molecule. The use of β-mannanase and α-galactosidase for synergistic hydrolysis of a GM with a high branching degree can reduce the negative influence of a galactose branched chain on hydrolysis of a GM backbone by β-mannanase, thereby increasing contents of small-molecule GM and GMOS components in the final degradation product.

The addition of α-galactosidase to mannanase to increase the contents of small-molecule GM and GMOS components in a degradation product is a focus of the current research. It needs to be implemented by a two-step method, that is, α-galactosidase and β-mannanase are acquired through microbial fermentation, and then α-galactosidase is added in a specified proportion to a system for hydrolyzing a GM by β-mannanase. If an enzyme solution with an optimal ratio of β-mannanase to α-galactosidase can be prepared by a one-step method, the production cost will be greatly reduced. In addition, the enzyme solution should be prepared with a human-safe microorganism, such as *Trichoderma reesei* (*T. reesei*). However, *T. reesei* also has an ability to synthesize β-mannosidase during the fermentation process to prepare α-galactosidase. Hence, when an enzyme solution with an optimal ratio of β-mannanase to α-galactosidase is prepared, an activity of β-mannosidase in the enzyme solution is required to be as low as possible, such that the enzyme solution obtained through fermentation can be directly used for production of a small-molecule GM and a GMOS without purification, which can further reduce a production cost. However, this technology currently does not have excellent achievements.

SUMMARY

In view of the problems in the prior art, a first technical problem to be solved by the present disclosure is to provide a preparation method of a special complex enzyme for hydrolyzing a GM to prepare a small-molecule GM and a GMOS, where fermentation is conducted with *T. reesei* as an enzyme-producing strain and microcrystalline cellulose (MCC) and/or melibiose as carbon sources to obtain an enzyme solution with excellent enzymatic activity ratio through a one-step fermentation process, which involves simple operations and greatly reduces a production cost. A second technical problem to be solved by the present disclosure is to provide a special complex enzyme for hydrolyzing a GM to prepare a small-molecule GM and a GMOS. An activity of β-mannosidase in the special complex enzyme is low, and thus the special complex enzyme can directly hydrolyze a GM to prepare a small-molecule GM and a GMOS without being purified to remove β-mannosidase. A third technical problem to be solved by the present disclosure is to provide a use of the special complex enzyme in enzymatic hydrolysis to prepare a small-molecule GM and a GMOS, where the special complex enzyme can effectively improve yields of the small-molecule GM and GMOS, reduces a production cost with promising application prospect.

To solve the above problems, the present disclosure adopts the following technical solutions:

A preparation method of a special complex enzyme for hydrolyzing a GM to prepare a small-molecule GM and a GMOS is provided, including: conducting fermentation with *T. reesei* as an enzyme-producing strain and MCC and melibiose as carbon sources; and after the fermentation is completed, treating a resulting culture solution to obtain the special complex enzyme for hydrolyzing a GM to prepare a small-molecule GM and a GMOS.

In the preparation method of a special complex enzyme for hydrolyzing a GM to prepare a small-molecule GM and a GMOS, a total concentration of the MCC and the melibiose is 20.0 g/L to 35.0 g/L.

In the preparation method of a special complex enzyme for hydrolyzing a GM to prepare a small-molecule GM and a GMOS, a concentration ratio of the MCC to the melibiose is 1:0.1 to 1:6.

In the preparation method of a special complex enzyme for hydrolyzing a GM to prepare a small-molecule GM and a GMOS, when the total concentration is 20.0 g/L, concentrations of the MCC and the melibiose are 15 g/L and 5 g/L, 10 g/L and 10 g/L, or 5 g/L and 15 g/L, respectively; when the total concentration is 25.0 g/L, concentrations of the MCC and the melibiose are 20 g/L and 5 g/L, 15 g/L and 10 g/L, 10 g/L and 15 g/L, or 5 g/L and 20 g/L, respectively; when the total concentration is 30.0 g/L, concentrations of the MCC and the melibiose are 25 g/L and 5 g/L, 20 g/L and 10 g/L, 15 g/L and 15 g/L, 10 g/L and 20 g/L, or 5 g/L and 25 g/L, respectively; and when the total concentration is 35.0 g/L, concentrations of the MCC and the melibiose are 30 g/L and 5 g/L, 25 g/L and 10 g/L, 20 g/L and 15 g/L, 15 g/L and 20 g/L, 10 g/L and 25 g/L, or 5 g/L and 30 g/L, respectively.

In the preparation method of a special complex enzyme for hydrolyzing a GM to prepare a small-molecule GM and a GMOS, a concentration of the MCC is 20 g/L, and a concentration of the melibiose is 5 g/L.

The preparation method of a special complex enzyme for hydrolyzing a GM to prepare a small-molecule GM and a GMOS includes the following steps:

(1) an enzyme-producing medium: including the following components: glucose: 1.0 g/L, a carbon source, ammonium sulfate: 4.72 g/L, urea: 2.15 g/L, monopotassium phosphate (MKP): 2.0 g/L, anhydrous calcium chloride: 0.3 g/L, magnesium sulfate heptahydrate: 0.3 g/L, ferrous sulfate heptahydrate: 0.005 g/L, manganese sulfate heptahydrate: 0.0016 g/L, zinc sulfate heptahydrate: 0.0014 g/L, and cobalt chloride: 0.002 g/L; and adding 50 mL of a sodium citrate buffer with a concentration of 1 mol/L to adjust a pH of the medium to 4.8; and (2) fermentation: adding 50 mL of the enzyme-producing medium to a 250 ml Erlenmeyer flask with a cotton stopper, inoculating *T. reesei* spores into the enzyme-producing medium at an inoculum size of 10%, and cultivating the *T. reesei* spores in a thermostatic shaker at 28° C. to 30° C. and 170 rpm for 4 d; and after the cultivation is completed, centrifuging a resulting culture solution at 3,000 rpm for 10 min to obtain a supernatant, which is the special complex enzyme for hydrolyzing a GM to prepare a small-molecule GM and a GMOS.

A special complex enzyme for hydrolyzing a GM to prepare a small-molecule GM and a GMOS prepared by the preparation method is provided.

A method for hydrolyzing a GM to prepare a small-molecule GM and a GMOS is provided, including the following steps:

1) conducting fermentation with MCC and melibiose as carbon sources and *T. reesei* as an enzyme-producing strain to obtain a supernatant, which is a complex enzyme solution with enzymatic activities of β-mannanase and α-galactosidase; and 2) directly using the complex enzyme solution obtained in step 1) for enzymatic hydrolysis of a GM as a substrate to prepare the small-molecule GM and the GMOS.

In step 1), a weight ratio of the MCC to the melibiose is 2:1, and an enzymatic activity ratio of the β-mannanase to the α-galactosidase is no less than 7.

In step 2), during the enzymatic hydrolysis, a substrate concentration is 2%, the complex enzyme solution is added at an amount of 20 U/g relative to the GM, and a pH is 4.8

Beneficial effects: Compared with the prior art, the present disclosure has the following advantages:

(1) In the present disclosure, fermentation is conducted with *T. reesei* as an enzyme-producing strain and MCC and melibiose as carbon sources and inducers to produce a special complex enzyme for hydrolyzing a GM to prepare a small-molecule GM and a GMOS; and a content (activity) of β-mannosidase in the special complex enzyme is not higher than 0.05 U/mL.

(2) Without being purified to remove β-mannosidase, the special complex enzyme prepared in the present disclosure can directly hydrolyze a GM to prepare a small-molecule GM and a GMOS, which can effectively improve yields of the small-molecule GM and GMOS and reduce a production cost.

(3) α-galactosidase is an enzyme that can specifically hydrolyze the α1,6-glycosidic bond formed between mannose and galactose in a GM molecule. The use of β-mannanase and α-galactosidase for synergistic hydrolysis of a GM with a high branching degree can reduce the negative influence of a galactose branched chain on hydrolysis of a GM backbone by β-mannanase, thereby increasing contents of small-molecule GM and GMOS components in the final degradation product.

DETAILED DESCRIPTION OF THE EMBODIMENTS

Figure 1:
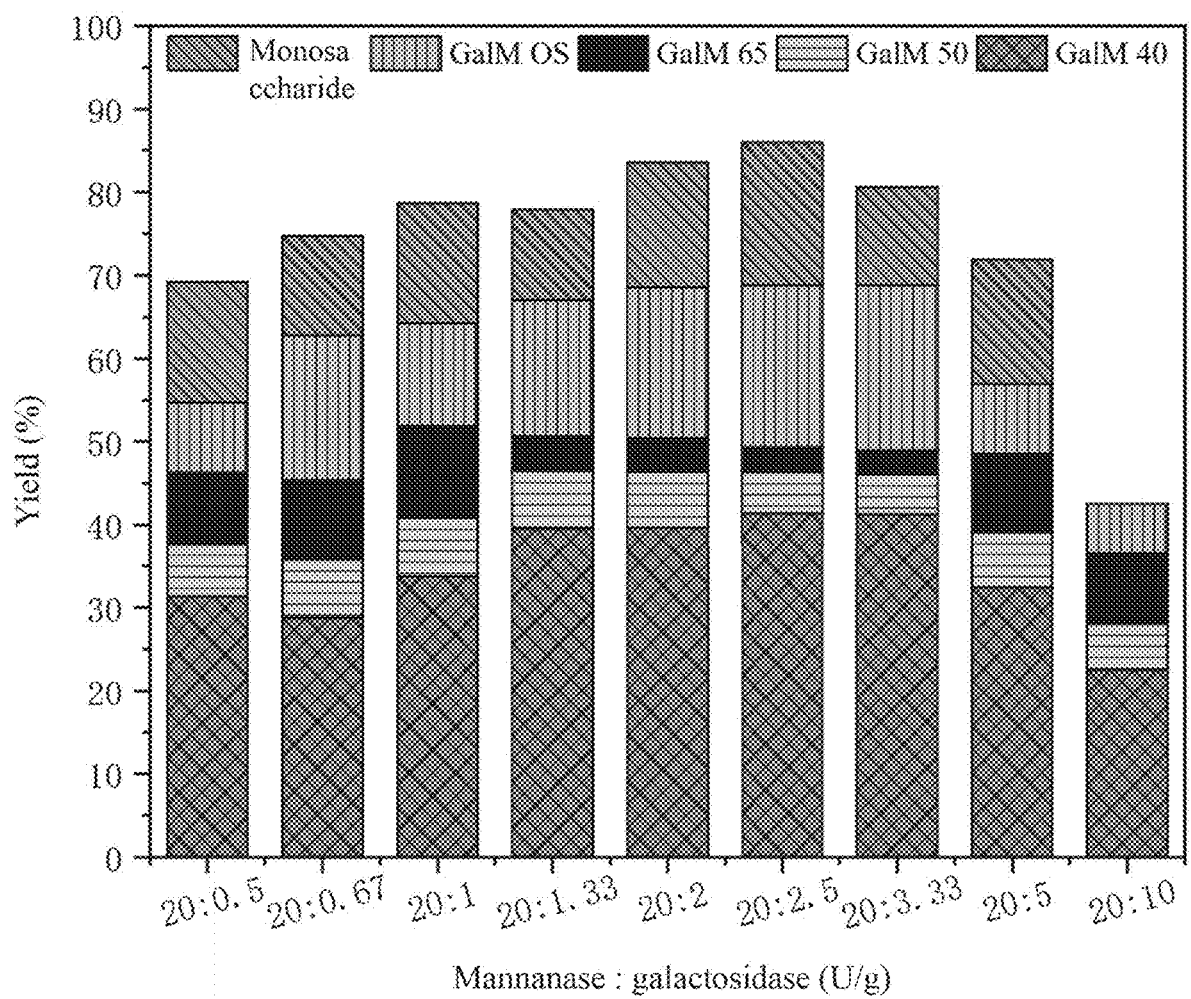
FIG. 1 shows results of enzymatic hydrolysis by a combination of β-mannanase and α-galactosidase.
Figure 2A:
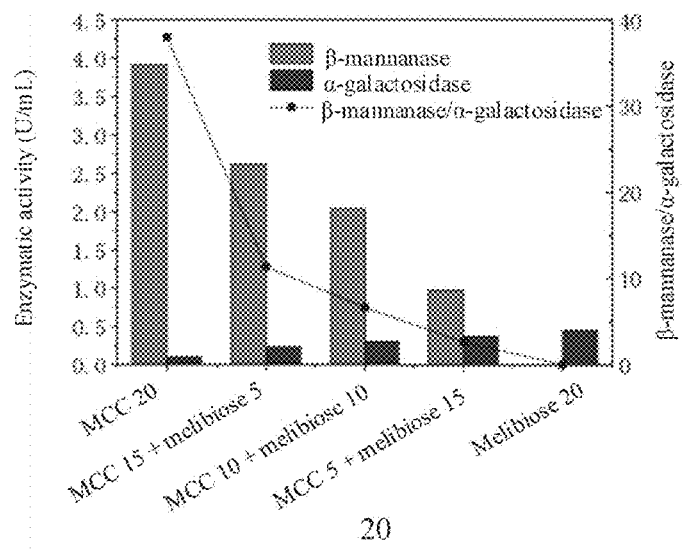
FIGS. 2A-2D show enzymatic activity results of β-mannanase and α-galactosidase at different MCC-to-melibiose ratios when a total substrate concentration is 20 g/L, 25 g/L, 30 g/L, and 35 g/L.
Figure 2B:
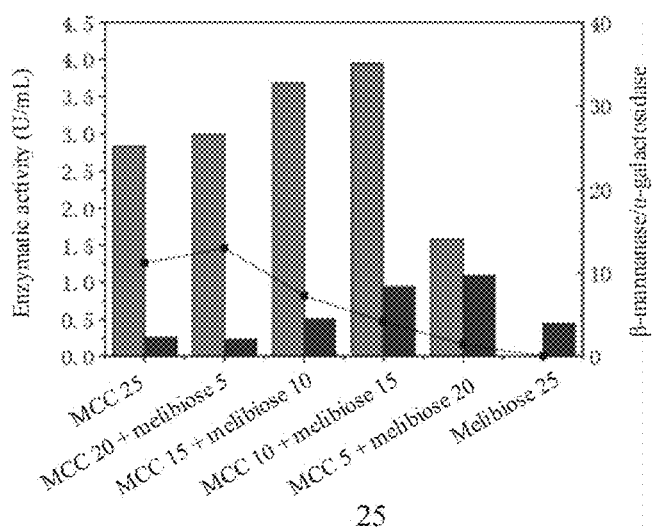
Figure 2C:
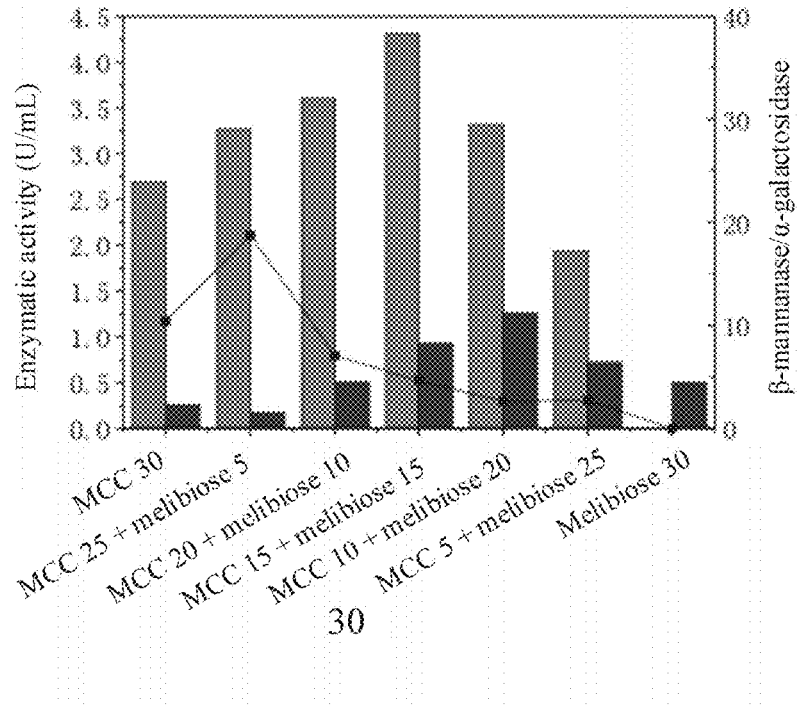
Figure 2D:
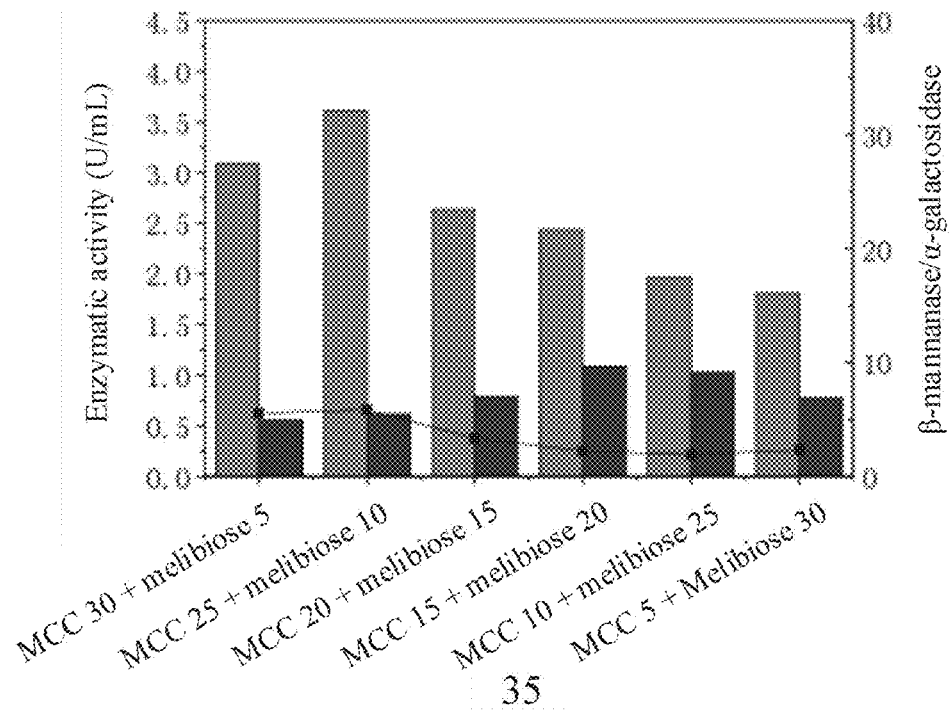

To make the objectives, features, and advantages of the present disclosure clear and comprehensible, specific implementations of the present disclosure will be described in detail below in conjunction with specific examples.

The performance of a product used in the following examples is tested as follows:

(1) A molecular weight distribution (MWD) is determined by gel permeation chromatography (GPC) for a small-molecule GM and a GMOS.

Chromatography conditions are as follows: chromatographic instrument: Agilent High-Performance liquid Chromatography (HPLC) 1260; chromatographic column: Waters Ultrahydrogel™ 2000 (7.8×300 mm), Waters Ultrahydrogel™ 250 (7.8×300 mm), and Waters Ultrahydrogel™ 120 (7.8×300 mm) sequentially connected in series; guard column: Waters Ultrahydrogel™ Guard Column (6×40 mm); detector: differential detector: mobile phase: water; mobile phase flow rate: 0.60 mL/min; column temperature: 65° C.; injection volume: 10.0 μL; and standard sample for molecular weight determination: polyethylene glycol (PEG).

(2) A saccharide content is determined by acid hydrolysis and ion chromatography for a small-molecule GM and a GMOS.

A determination method is as follows: 0.3 g of a small-molecule GM and GMOS sample is taken and added to a hydrolysis flask, 87 mL of 4% $H_2SO_4$ is added, and a reaction is conducted at 121° C. for 1 h; after the reaction is completed, 1 mL of a reaction solution is collected, and a pH of the reaction solution is adjusted with 50% NaOH to 7.0: the reaction solution is centrifuged at 10,000 rpm for 5 min, and a resulting supernatant is collected; and finally an ICS-5000 ion exchange chromatograph is used to determine concentrations of mannose and galactose in the supernatant.

Ion chromatography conditions are as follows: chromatographic instrument: Dionex ion chromatography ICS-5000; chromatographic column: 2×250 mm Dionex AminoPac PA10; guard column: 2×50 mm Dionex AminoPac PA10 detector: conductivity detector; mobile phase: 3 mmol sodium hydroxide; flow rate: 0.20 mL min; column temperature: 30° C.; injection volume: 10.0 μL; and determination is conducted by an external standard method. Purities of a small-molecule GM and a GMOS in a sample are calculated as follows:

$$GM \text{ degradation product content} = \frac{(\text{Galactose concentration} + \text{mannose concentration}) \times 0.9 \times 0.087}{0.3} \times 100\%$$

(3) Determination of an activity of β-mannanase:

0.9 mL of a 5 g/L locust bean gum substrate solution is added to a 25 mL graduated test tube and pre-heated at 50° C. for 5 min, 0.1 mL of an appropriately-diluted enzyme solution is added, and a reaction is conducted at 50° C. for 30 min; 3.0 mL of a DNS reagent is immediately added to terminate the reaction, and a resulting reaction solution is treated in a boiling water bath for 7 min, cooled, diluted to 25 mL, and thoroughly shaken; the absorbance of the reaction solution is determined at 540 nm; and according to a correlationship between the absorbance and a reducing sugar, a concentration of the reducing sugar generated is calculated. One activity unit (U) of β-mannanase is calculated according to an amount of β-mannanase required for hydrolysis of a substrate to produce 1 μmol of a reducing sugar (based on mannose) per minute.

(4) Determination of an activity of α-galactosidase:

0.1 mL of an appropriately-diluted enzyme solution and 0.9 mL of a 1 mmol/L p-nitrophenol-α-D-galactopyranoside (pNPG) solution are added to a 15 mL test tube and incubated at 50° C. for 10 min, and then 2.0 mL of a 1 mol/L $Na_2CO_3$ solution is immediately added to terminate a reaction; 10 mL of distilled water is added, and a resulting reaction solution is thoroughly shaken; the absorbance of the reaction solution is determined at 400 nm; and according to a correlationship between the absorbance and p-nitrophenol, a concentration of the p-nitrophenol generated is calculated. One activity unit (U) of α-galactosidase is calculated according to an amount of α-galactosidase required for hydrolysis of pNPG to release 1 μmol of p-nitrophenol per minute.

(5) Determination of an activity of β-mannosidase:

0.1 mL of an appropriately-diluted enzyme solution and 0.9 mL of a 1 mmol/L p-nitrophenol-β-D-mannopyranoside (pNPM) solution are added to a 15 mL test tube and incubated at 50° C. for 10 min, and then 2.0 mL of a 1 mol/L $Na_2CO_3$ solution is immediately added to terminate a reaction; 10 mL of distilled water is added, and a resulting reaction solution is thoroughly shaken; the absorbance of the reaction solution is determined at 400 nm; and according to a correlationship between the absorbance and p-nitrophenol, a concentration of the p-nitrophenol generated by enzymatic hydrolysis is calculated. One activity unit (U) of β-mannosidase is calculated according to an amount of β-mannosidase required for hydrolysis of pNPM to release 1 μmol of p-nitrophenol per minute.

Example 1

Fermentation was conducted with *T. reesei* as an enzyme-producing strain and MCC or melibiose as carbon sources to produce an enzyme, including the following steps:

(1) Composition of an enzyme-producing medium (g/L): glucose: 1.0, MCC or melibiose: 25.0, ammonium sulfate: 4.72, urea: 2.15, MKP: 2.0, anhydrous calcium chloride: 0.3, magnesium sulfate heptahydrate: 0.3, ferrous sulfate heptahydrate: 0.005, manganese sulfate heptahydrate: 0.0016, zinc sulfate heptahydrate: 0.0014, and cobalt chloride: 0.002. 50 mL of a 1 mol/L sodium citrate buffer was added to adjust a pH of the medium to 4.8.

(2) Fermentation to Produce the Enzyme 50 mL of the medium was added to a 250 ml Erlenmeyer flask with a cotton stopper, and *T. reesei* spores were inoculated into the medium at an inoculum size of 10% and cultivated in a thermostatic shaker at 28° C. to 30° C. and 170 rpm for 4 d; and after the cultivation was completed, a resulting culture solution was centrifuged at 3,000 rpm for 10 min to obtain a supernatant (enzyme solution), and enzymatic activities of α-galactosidase, β-mannosidase, and β-mannanase were determined.

Results showed that, in enzyme solution 1 produced through fermentation with *T. reesei* as an enzyme-producing strain and MCC as a carbon source, an enzymatic activity of β-mannanase was 3.917 U/mL, an enzymatic activity of α-galactosidase was 0.099 U/mL, and an enzymatic activity of β-mannosidase was 0.02 U/mL; and in enzyme solution 2 produced through fermentation with *T. reesei* as an enzyme-producing strain and melibiose as a carbon source, an enzymatic activity of α-galactosidase was 0.452 U/mL.

Example 2

A small-molecule GM and a GMOS were prepared through enzymatic hydrolysis by a combination of mannanase and galactosidase, specifically including the following steps:

(1) Directed Enzymatic Hydrolysis of a GM

GM-containing leguminous seeds (*sesbania*) were mechanically crushed to 20-100 mesh, distilled water was added according to a solid-to-liquid ratio of 1:50, and extraction was conducted at 50° C. for 24 h; a resulting extraction solution was centrifuged at 10,000 rpm for 10 min; a resulting supernatant was collected, and absolute ethanol was added to the supernatant; and a resulting precipitate was vacuum-dried to obtain a GM powdered solid.

The enzyme solution 1 and the enzyme solution 2 obtained in Example 1 were mixed to allow the following enzymatic activity ratios of β-mannanase to α-galactosidase: 2, 4, 6, 8, 10, 12, 15, 20, 30, and 40. Then, 20.0 g of the GM was weighed and added to a 2 L enzyme reaction tank, distilled water, an enzyme solution, and a 1 mol/L citric acid buffer were added in the tank to obtain 1,000 mL of a reaction solution: the reaction solution was thoroughly mixed, and a reaction was conducted for 24 h under the following conditions: substrate concentration: 2%, enzyme amount relative to the GM: 20 U/g, pH: 4.8, and temperature: 50° C.; and after the enzymatic hydrolysis reaction was completed, an enzymatic hydrolysate was treated at 100° C. for 10 min to inactivate enzymes, and an inactivated enzymatic hydrolysate was centrifuged at 10,000 rpm for 10 min to obtain a supernatant, which was an enzymatic hydrolysate including the small-molecule GM and the GMOS.

(2) 1,000 mL of the enzymatic hydrolysate including the small-molecule GM and the GMOS obtained in step (1) was taken, absolute ethanol was added under stirring until an ethanol concentration in a resulting system was 40% (v/v), and the system was centrifuged at 10,000 rpm for 10 min to obtain a supernatant and a precipitate; the precipitate was washed 3 times with a 40% (v/v) ethanol aqueous solution, collected through centrifugation at 10,000 rpm for 10 min, and lyophilized to obtain a small-molecule GM component named GalM40: a molecular weight of the small-molecule GM component GalM40 was determined by gel chromatography, and a content of a GM degradation product was determined by acid hydrolysis and ion chromatography: and the supernatant was further used for the next fractionation.

(3) The supernatant obtained after solid-liquid separation (SLS) in step (2) was taken, absolute ethanol was added under stirring until an ethanol concentration in a resulting system was 50% (v/v), and the system was centrifuged at 10,000 rpm for 10 min to obtain a supernatant and a precipitate; the precipitate was washed 3 times with a 50% (v/v) ethanol aqueous solution, collected through centrifugation at 10,000 rpm for 10 min, and lyophilized to obtain a small-molecule GM component named GalM50; a molecular weight of the small-molecule GM component GalM50 was determined by gel chromatography, and a content of a GM degradation product was determined by acid hydrolysis and ion chromatography; and the supernatant was further used for the next fractionation.

(4) The supernatant obtained after SLS in step (3) was taken, absolute ethanol was added under stirring until an ethanol concentration in a resulting system was 65% (v/v) and the system was centrifuged at 10,000 rpm for 10 min to obtain a supernatant and a precipitate: the precipitate was washed 3 times with a 65% (v/v) ethanol aqueous solution, collected through centrifugation at 10,000 rpm for 10 min, and lyophilized to obtain a small-molecule GM component named GalM65; a molecular weight of the small-molecule GM component GalM65 was determined by gel chromatography, and a content of a GM degradation product was determined by acid hydrolysis and ion chromatography: and the supernatant was further used for the next fractionation.

(5) The supernatant obtained after SLS in step (4) was taken and subjected to vacuum rotary evaporation at 70° C. and 160 mbar to remove ethanol; a part of a resulting supernatant was taken, and a content of a GM degradation product in the supernatant was determined by acid hydrolysis and ion chromatography; monosaccharides in the remaining part of the supernatant were removed through nanofiltration (200 Da), then a resulting filtrate was concentrated through vacuum rotary evaporation at 70° C. and 160 mbar to obtain a concentrate; and the concentrate was dried to obtain a GMOS component GalMOS, and a molecular weight of the GMOS component GalMOS was determined by gel chromatography.

FIG. 1 shows results of enzymatic hydrolysis by a combination of β-mannanase and α-galactosidase. It can be seen from FIG. 1 that, at an early stage, with the continuous increase of an enzymatic activity of α-galactosidase, a total yield of the three small-molecule GMs GalM40, GalM50, and GalM65 and a yield of GalMOS tend to increase slowly, and a total yield of saccharides also tends to increase slowly; and at a later stage, with the further increase of an enzymatic activity of α-galactosidase, a total yield of the three small-molecule GMs GalM40, GalM50, and GalM65 and a yield of GalMOS start to decrease, and a total yield of saccharides also starts to decrease. It can be seen from FIG. 1 that, when an enzymatic activity ratio of β-mannanase to α-galactosidase is 8, a total yield of saccharides is the highest, and a total yield of the three small-molecule GMs GalM40, GalM50, and GalM65 and a yield of GalMOS are also the highest. In addition, a molecular weight of a small-molecule GM obtained was measured, and an average molecular weight of each component was as follows: GalM40: 13,100 Da, GalM50: 8,930 Da, GalM65: 4,310 Da, and GalMOS: 1,630 Da.

Example 3

An enzyme was prepared with a combination of MCC and melibiose, including the following steps:

(1) An enzyme-producing medium was the same as in Example 1. The substrate was replaced by a mixture of MCC and melibiose in different ratios, where a total concentration of the two substrates was 20.0 g/L, 25.0 g/L, 30.0 g/L, and 35.0 g/L.

(2) An enzyme-producing fermentation method was the same as in Example 1.

Results were shown in FIGS. 2A-2D. When a total substrate concentration is 20 g/L, an activity of β-mannanase continuously decreases with the continuous increase of melibiose. However, when a total substrate concentration is 25 g/L, 30 g/L, and 35 g/L, an enzymatic activity of β-mannanase tends to increase first and then decrease with the continuous increase of melibiose. When a total substrate concentration is 25 g/L with an MCC concentration of 20 g/L and a melibiose concentration of 5 g/L, an enzymatic activity ratio of β-mannanase to α-galactosidase is the highest. In general, an enzymatic activity of α-galactosidase continuously increases with the increase of melibiose; and when a melibiose concentration is too high, an enzymatic activity of α-galactosidase gradually decreases.

Example 4

A method for preparing a small-molecule GM and a GMOS through enzymatic hydrolysis with an enzyme solution produced by a combination of MCC and melibiose was provided, including the following steps:

directed enzymatic hydrolysis of a GM was the same as in Example 2, where an enzyme solution used was the enzyme solution in Example 3; and enzyme solutions with different enzymatic activity ratios of β-mannanase to α-galactosidase were used to conduct an enzymatic hydrolysis test.

Figure 3:
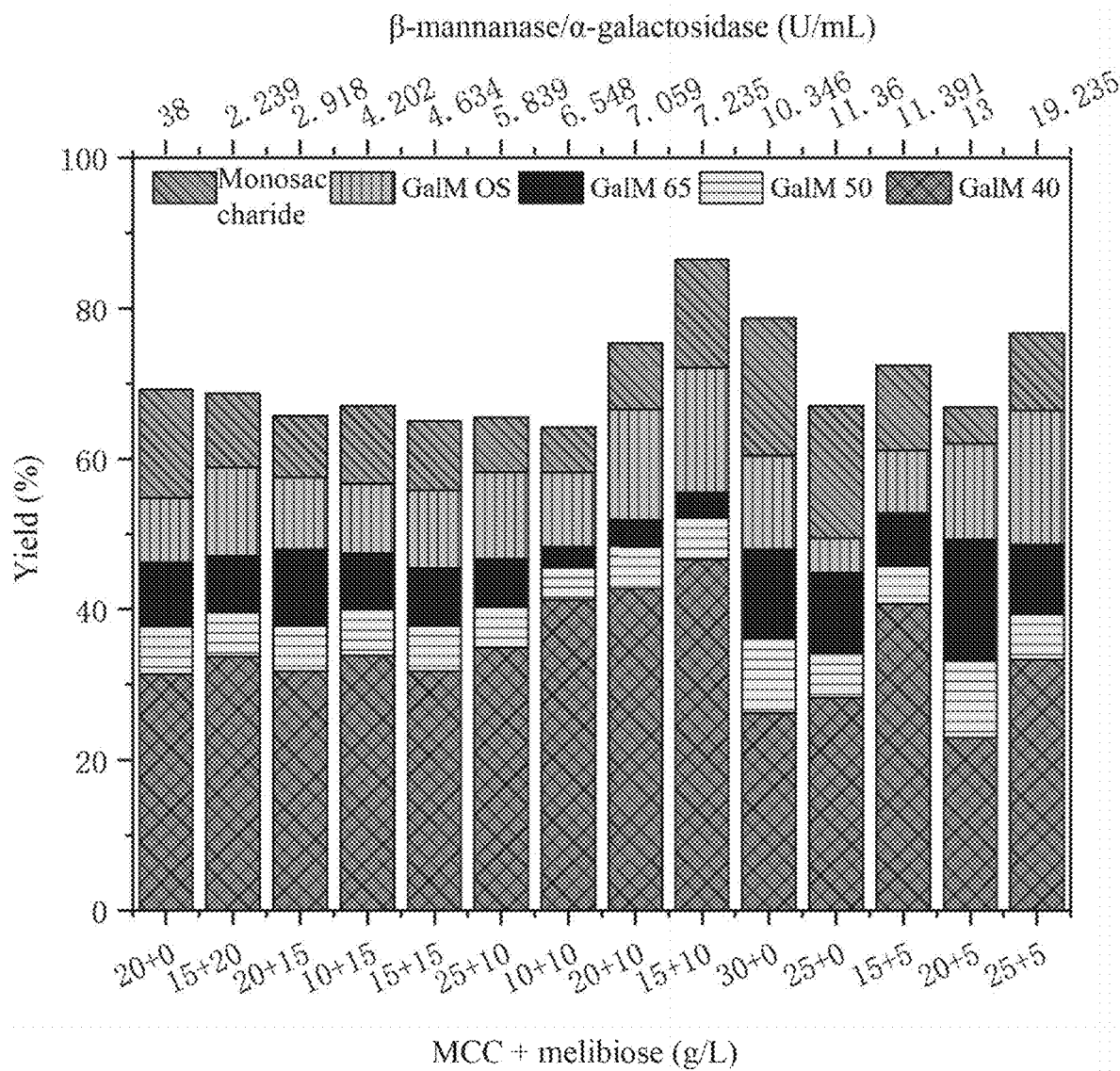
FIG. 3 shows enzymatic hydrolysis results of enzyme solutions with different enzymatic activity ratios of β-mannanase to α-galactosidase.

Results were shown in FIG. 3. An enzyme solution produced with 15 g/L MCC and 10 g/L melibiose has the optimal enzymatic hydrolysis effect, where a total yield of saccharides is 86.47%, a yield of GalM OS is 16.51%, a total yield of the three small-molecule GMs GalM40, GalM50, and GalM65 is 55.63%, and an enzymatic activity ratio of β-mannanase to α-galactosidase is 7.235. These results correspond to the results of the previous enzymatic hydrolysis by the combination of β-mannanase and α-galactosidase.

What is claimed is:

1. A preparation method of an enzyme solution for hydrolyzing a galactomannan (GM) to prepare a small-molecule GM and a galactomannan oligosaccharide (GMOS), wherein the enzyme solution comprises enzymatic activities of β-mannanase and α-galactosidase, wherein an enzymatic activity ratio of the of the β-mannanase to the α-galactosidase is no less than 7:1, and wherein the small-molecule GM has a molecular weight of 20,000 Da or less, comprising:

conducting a fermentation with *Trichoderma reesei* (*T. reesei*) as an enzyme-producing strain and microcrystalline cellulose (MCC) and melibiose as carbon sources, wherein the total concentration of the MCC and the melibiose is 20.0 g/L to 35.0 g/L; and after the fermentation is completed, centrifuging a resulting culture solution, wherein the supernatant comprises the enzyme solution for hydrolyzing the GM to prepare the small-molecule GM and the GMOS.

2. The preparation method of the enzyme solution for hydrolyzing the GM to prepare the small-molecule GM and the GMOS according to claim 1, wherein a concentration ratio of the MCC to the melibiose is 1:0.1 to 1:6.

3. The preparation method of the enzyme solution for hydrolyzing the GM to prepare the small-molecule GM and the GMOS according to claim 1, wherein when a total concentration is 20.0 g/L, concentrations of the MCC and the melibiose are 15 g/L and 5 g/L, 10 g/L and 10 g/L, or 5 g/L and 15 g/L, respectively; wherein when the total concentration is 25.0 g/L, concentrations of the MCC and the melibiose are 20 g/L and 5 g/L, 15 g/L and 10 g/L, 10 g/L and 15 g/L, or 5 g/L and 20 g/L, respectively; wherein when the total concentration is 30.0 g/L, concentrations of the MCC and the melibiose are 25 g/L and 5 g/L, 20 g/L and 10 g/L, 15 g/L and 15 g/L, 10 g/L and 20 g/L, or 5 g/L and 25 g/L, respectively; and wherein when the total concentration is 35.0 g/L, concentrations of the MCC and the melibiose are 30 g/L and 5 g/L, 25 g/L and 10 g/L, 20 g/L and 15 g/L, 15 g/L and 20 g/L, 10 g/L and 25 g/L, or 5 g/L and 30 g/L, respectively.

4. The preparation method of the enzyme solution for hydrolyzing the GM to prepare the small-molecule GM and the GMOS according to claim 1, wherein a concentration of the MCC is 20 g/L, and a concentration of the melibiose is 5 g/L.

5. The preparation method of the enzyme solution for hydrolyzing the GM to prepare the small-molecule GM and the GMOS according to claim 1, comprising the following steps:

(1) an enzyme-producing medium: comprising the following components: glucose: 1.0 g/L, MCC and melibiose, ammonium sulfate: 4.72 g/L, urea: 2.15 g/L, monopotassium phosphate (MKP): 2.0 g/L, anhydrous calcium chloride: 0.3 g/L, magnesium sulfate heptahydrate: 0.3 g/L, ferrous sulfate heptahydrate: 0.005 g/L, manganese sulfate heptahydrate: 0.0016 g/L, zinc sulfate heptahydrate: 0.0014 g/L, and cobalt chloride: 0.002 g/L; and adding 50 mL of a sodium citrate buffer with a concentration of 1 mol/L to adjust a pH of the enzyme-producing medium to 4.8; and (2) the fermentation: adding 50 mL of the enzyme-producing medium to a 250 ml Erlenmeyer flask with a cotton stopper, inoculating T. reesei spores into the enzyme-producing medium at an inoculum size of 10%, and cultivating the *T. reesei* spores in a thermostatic shaker at 28° C. to 30° C. and 170 rpm for 4 d; and after a cultivation is completed, centrifuging the resulting culture solution at 3,000 rpm for 10 min to obtain a supernatant, which is the enzyme solution for hydrolyzing the GM to prepare the small-molecule GM and the GMOS.

6. A method for hydrolyzing a GM to prepare a small-molecule GM and a GMOS, wherein the small-molecule GM has a molecular weight of 20,000 Da or less, comprising the following steps:

1) conducting a fermentation with MCC and melibiose as carbon sources and *T. reesei* as an enzyme-producing strain to obtain a supernatant, which is an enzyme solution with enzymatic activities of β-mannanase and α-galactosidase, wherein an enzymatic activity ratio of the of the β-mannanase to the α-galactosidase is no less than 7:1, and wherein the total concentration of the MCC and the melibiose is 20.0 g/L to 35.0 g/L; and after the fermentation is completed, centrifuging a resulting culture solution, wherein the supernatant comprises the enzyme solution; and 2) directly using the enzyme solution obtained in step 1) for an enzymatic hydrolysis of the GM as a substrate to prepare the small-molecule GM and the GMOS.

7. The method for hydrolyzing the GM to prepare the small-molecule GM and the GMOS according to claim 6, wherein in step 1), a weight ratio of the MCC to the melibiose is 2:1.

8. The method for hydrolyzing the GM to prepare the small-molecule GM and the GMOS according to claim 6, wherein in step 2), during the enzymatic hydrolysis, a substrate concentration is 2%, the enzyme solution is added at an amount of 20 U/g relative to the GM, and a pH is 4.8.

* * * * *